United States Patent [19]

Patel

[11] 4,384,980
[45] May 24, 1983

[54] CO-CRYSTALLIZED ACETYLENIC COMPOUNDS

[75] Inventor: Gordhanbhai N. Patel, Morris Plains, N.J.

[73] Assignee: Allied Corporation, Morris Township, Morris County, N.J.

[21] Appl. No.: 960,508

[22] Filed: Nov. 13, 1978

Related U.S. Application Data

[62] Division of Ser. No. 960,508, Nov. 13, 1978, which is a division of Ser. No. 817,069, Jul. 19, 1977, Pat. No. 4,189,399.

[51] Int. Cl.$^3$ .............................................. C09K 3/00
[52] U.S. Cl. ...................................... 436/58; 116/202; 116/207; 427/270; 427/283; 204/159.22; 436/147; 436/164; 436/905
[58] Field of Search .................... 252/408, 300, 600; 73/356; 427/270, 283; 116/202, 207; 426/88; 250/474; 204/159.22

[56] References Cited

U.S. PATENT DOCUMENTS

| | | | |
|---|---|---|---|
| 3,501,308 | 3/1970 | Adelman | 96/88 |
| 3,615,719 | 10/1971 | Michel et al. | 426/88 |
| 3,811,895 | 5/1974 | Ehrlich | 96/88 |
| 3,999,946 | 12/1976 | Patel et al. | 252/408 |

*Primary Examiner*—J. L. Barr
*Attorney, Agent, or Firm*—Alan M. Doernberg; Kenneth E. Stroup, Jr.; Gerhard H. Fuchs

[57] ABSTRACT

A composition is described comprising at least two co-crystallized acetylenic compounds, of different chemical structures, each containing at least one —C≡C—C≡C— group and substituents selected from the group consisting of sulfonate, urethane and alcohol radicals, at least one of the compounds capable of undergoing a contrasting color change upon exposure to actinic radiation or thermal annealing, wherein the composition exhibits a substantially different thermogram than the sum of thermograms of the individual components as obtained by differential scanning alorimetry.

A device is also described useful for measuring the time-temperature or radiation-dosage history of an article comprising a substrate having deposited thereon the described composition.

A process is also described for producing the composition of this invention.

3 Claims, 4 Drawing Figures

THERMAL ANNEALING CHARACTERISTICS OF CO-CRYSTALLIZED COMPOSITIONS CONTAINING HDDPU AND HDDPBPU IN DIFFERENT PROPORTIONS

| THERMAL ANNEALING TIME AT 80°C | | | | | | | | | | |
|---|---|---|---|---|---|---|---|---|---|---|
| 80 hr | 5 | 6 | 7 | 7 | 7 | 7 | 7 | 7 | 7 | 7 |
| 50 hr | 4 | 5 | 6 | 7 | 7 | 7 | 7 | 7 | 7 | 7 |
| 30 hr | 4 | 5 | 5 | 6 | 7 | 7 | 7 | 7 | 7 | 7 |
| 20 hr | 4 | 5 | 5 | 5 | 6 | 7 | 7 | 7 | 7 | 7 |
| 14 hr | 3 | 4 | 5 | 5 | 5 | 6 | 7 | 7 | 7 | 7 |
| 8 hr | 3 | 3 | 4 | 4 | 5 | 5 | 7 | 7 | 7 | 7 |
| 5.0 hr | 2 | 3 | 3 | 3 | 4 | 5 | 7 | 7 | 7 | 7 |
| 3.0 hr | 2 | 3 | 3 | 3 | 4 | 4 | 6 | 7 | 6 | 6 |
| 1.5 hr | 2 | 2 | 2 | 3 | 3 | 4 | 6 | 7 | 6 | 4 |
| 50 mins | 1 | 2 | 2 | 2 | 3 | 3 | 5 | 6 | 5 | 3 |
| 30 mins | 1 | 1 | 2 | 2 | 3 | 3 | 5 | 5 | 4 | 2 |
| 10 mins | 1 | 1 | 2 | 2 | 3 | 3 | 5 | 4 | 4 | 1 |
| | 100 | 99.5 | 99 | 98 | 97 | 95 | 90 | 80 | 70 | 60 |

CONCENTRATION OF HDDPU (% BY WEIGHT)

COLOR TABLE:

- 7 = METALLIC (GREEN-GOLD OR RUSTY-RED).
- 6 = TRANSITION COLOR BETWEEN DARK VIOLET AND METALLIC.
- 5 = DARK VIOLET.
- 4 = VIOLET.
- 3 = REDDISH VIOLET.
- 2 = LIGHT REDDISH VIOLET.
- 1 = PINK.

FIG. 4

CO-CRYSTALLIZED ACETYLENIC COMPOUNDS

This is a division of application Ser. No. 960,508 filed Nov. 13, 1978, which in turn is a division of application Ser. No. 817,069 filed July 19, 1977, now U.S. Pat. No. 4,189,399, issued Feb. 19, 1980.

CROSS-REFERENCES TO RELATED APPLICATIONS

The subject matter of this application was disclosed but not claimed in a prior application, U.S. application Ser. No. 660,562, filed Feb. 23, 1976 by the present inventor and others, which issued as U.S. Pat. No. 3,999,946 on Dec. 28, 1976.

BACKGROUND OF THE INVENTION

1. Field of the Invention

This invention relates to novel co-crystallized compositions comprising at least two acetylenic compounds, useful in measuring the time-temperature or radiation-dosage history of an article.

2. Brief Description of the Prior Art

Radiation sensitive compositions containing a polyacetylenic compound, having a minimum of two conjugated acetylenic linkages, commingled with an organic pi-acid electron acceptor are described in U.S. Pat. No. 3,501,308 (Adelman, 1970). However, compositions comprising at least two acetylenic compounds, each containing at least one —C≡C—C≡C— group, are not described by the reference.

Image-receptive elements containing fixed position photosensitive crystals of polyacetylenic compounds, having at least two acetylenic linkages in a conjugated system, are described in U.S. Pat. No. 3,501,297 (Creamens, 1970). Reference is made to a mixture of 11,13-tetracosadiynedioic acid containing up to about 20 to 30 percent of monoethyl ester of 11,13-tetracosadiynedioic acid useful in an image-receptive element, but no properties are described to suggest that the compounds in the composition are co-crystallized compounds rather than being a simple mixture.

Acetylenic compounds having at least two conjugated C C groups have been disclosed as time-temperature history indicators in U.S. Pat. No. 3,999,946. Monomeric acetylenic compounds, of the formula, R—C≡C—C≡C—R, where R is a monovalent radical, are colorless and are polymerizable in the solid state, either thermally or by actinic radiation. As the polymerization proceeds, these compounds undergo a contrasting color change to blue or pink and the color intensifies with time until the compounds finally develop into metallic-looking polymers. Thus, the compounds can be used as time-temperature history indicators and as radiation-dosage indicators. The reference also describes polymers of the type [C≡C—(CH$_2$)$_m$OCONH(CH$_2$)$_6$NHOCO(CH$_2$)$_m$—C≡C]$_n$ where m is 2, 3 or 4 and n is large, wherein a polymer containing polymeric repeating units of the same empirical formula, undergo color changes upon thermal annealing.

SUMMARY OF THE INVENTION

It has been unexpectedly found that by dissolving in a solvent two or more acetylenic compounds, of different chemical structures, each containing at least one —C≡C—C≡C— group, and either removing the solvent therefrom at such rate that it exceeds the rate of initiating crystallization of each acetylenic compound separately, or mixing the solution with a liquid which is miscible with the solvent but acts as a nonsolvent for the co-crystallized composition, at such rate that mixing is complete before the initiation time for crystallization of each acetylenic compound separately from the same solvent mixture, a co-crystallized composition of the two acetylenic compounds is obtained in which the thermogram of the composition is different from the sum of the thermograms of the individual components as measured by differential scanning calorimetry. The obtained co-crystallized compositions exhibit surprisingly different reactivity rates of color change upon exposure to actinic radiation or thermal annealing than the individual components. Thus, the applicable range of utility of acetylenic compounds can be extensively varied for use in measuring the time-temperature or radiation-dosage history of an article.

In accordance with this invention, there is provided a composition comprising at least two co-crystallized acetylenic compounds, of different chemical structures, each containing at least one —C≡C—C≡C— group and substituents selected from the group consisting of sulfonate, urethane and alcohol radicals, at least one of the compounds capable of undergoing a contrasting color change upon exposure to actinic radiation or thermal annealing, wherein the composition exhibits a substantially different thermogram than the sum of the thermograms of the individual components as obtained by differential scanning calorimetry.

A device is also provided useful for measuring the time-temperature or radiation-dosage history of an article comprising a substrate having deposited thereon at least one of the compositions of the invention.

Further provided is a device for measuring temperature comprising a substrate having deposited thereon at least one thermochromic co-crystallized composition.

A process for making the compositions of this invention is also provided which comprises the steps of
(a) dissolving at least two acetylenic compounds in a solvent therefor, thereby forming a solution; and
(b) recovering the co-crystallized composition from the solution by removal of the solvent at such rate that it exceeds the rate of initiating crystallization of each acetylenic compound separately.

Another process for making the compositions of this invention is also provided which comprises the steps of
(a) dissolving at least two acetylenic compounds in a solvent therefor, thereby forming a solution;
(b) mixing the solution with a liquid, which is miscible with the solvent but is non-solvent for the co-crystallized composition, at such rate that mixing is complete before the initiation time for crystallization of each acetylenic compound separately from the same solvent mixture.

Another process is provided for making the compositions of this invention directly in a solvent which comprises the steps of
(a) reacting one or more acetylenic diols with one or more isocyanates or organic sulfonic acid agents, such that the total of different diols and isocyanates or organic sulfonic agents is at least three; and
(b) recovering the co-crystallized composition from the solution.

Further provided is a process for making the compositions of the invention which comprises the steps of (a) vaporizing at least two acetylenic compounds and (b) depositing the resulting vapor onto a substrate.

There is also provided a process for making the compositions of this invention which comprises the steps of (a) forming a melt of at least two acetylenic compounds and (b) cooling the melt rapidly.

Also provided is a copolymeric composition comprising an irradiated or thermally annealed product of a composition comprised of at least two co-crystallized acetylenic compounds, of different chemical structures, each containing at least one —C≡C—C≡C— group and substituents selected from the group consisting of sulfonate, urethane, and alcohol radicals, at least one of the compounds capable of undergoing a contrasting color change upon exposure to actinic radiation or thermal annealing, wherein the composition exhibits a substantially different thermogram than the sum of thermograms of the individual components as obtained by differential scanning calorimetry.

Further provided is a shaped article produced from the above copolymeric composition which possesses a decomposition temperature of at least about 20° C. above its melting point.

BRIEF DESCRIPTION OF THE DRAWINGS

FIG. 4 is a sequential array illustrating the differences in reactivity of color change, during thermal annealing at 80° C. for different exposure times, of a series of co-crystallized compositions of HDDPU and HDDPBPU containing varying weight concentrations of HDDPU. The individual squares are comprised of filter paper coated with the designated composition and which were individually thermally annealed for the indicated times at 80° C. The squares were then assembled to form a sequential array and were visually inspected by comparing developed colors of each square with others in the array and assigned a comparative number corresponding to the developed color as listed in the comparative Color Table. Proceeding vertically upward in each column, which represents one specific composition, the first square to read 7, designating the end-point color, represents the time variable used as the experimental point to form the curve in FIG. 3.

DESCRIPTION OF THE INVENTION AND PREFERRED EMBODIMENTS

Figure 1:
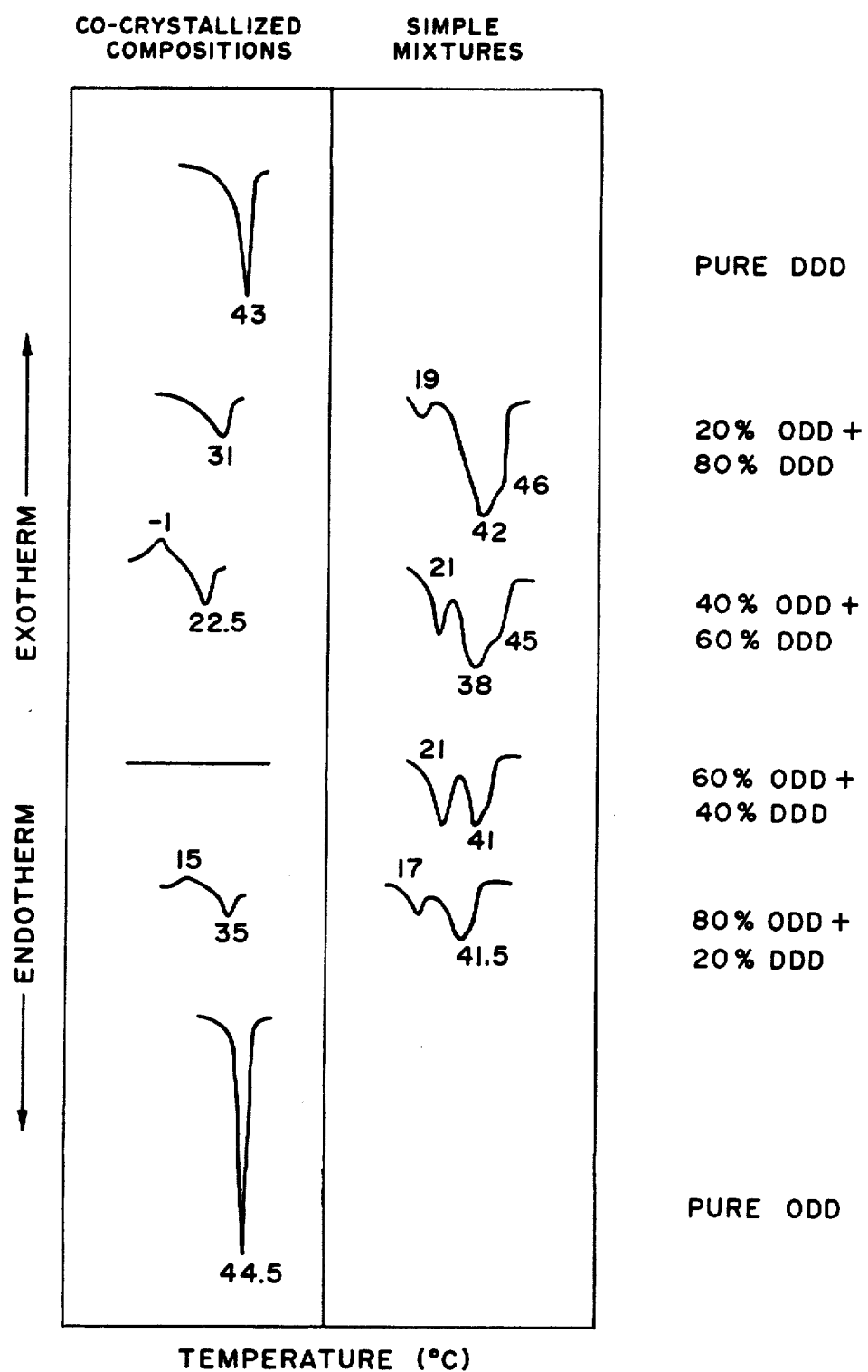
FIG. 1 illustrates thermograms, obtained by differential scanning calorimetry, of 3,5-octadiyn-1,8-diol (ODD) and 4,6-decadiyn-1,10-diol (DDD) as pure materials, individually, and, as co-crystallized compositions and simple mixtures thereof containing 20, 40, 60 and 80 weight percent of each component.
Figure 2:
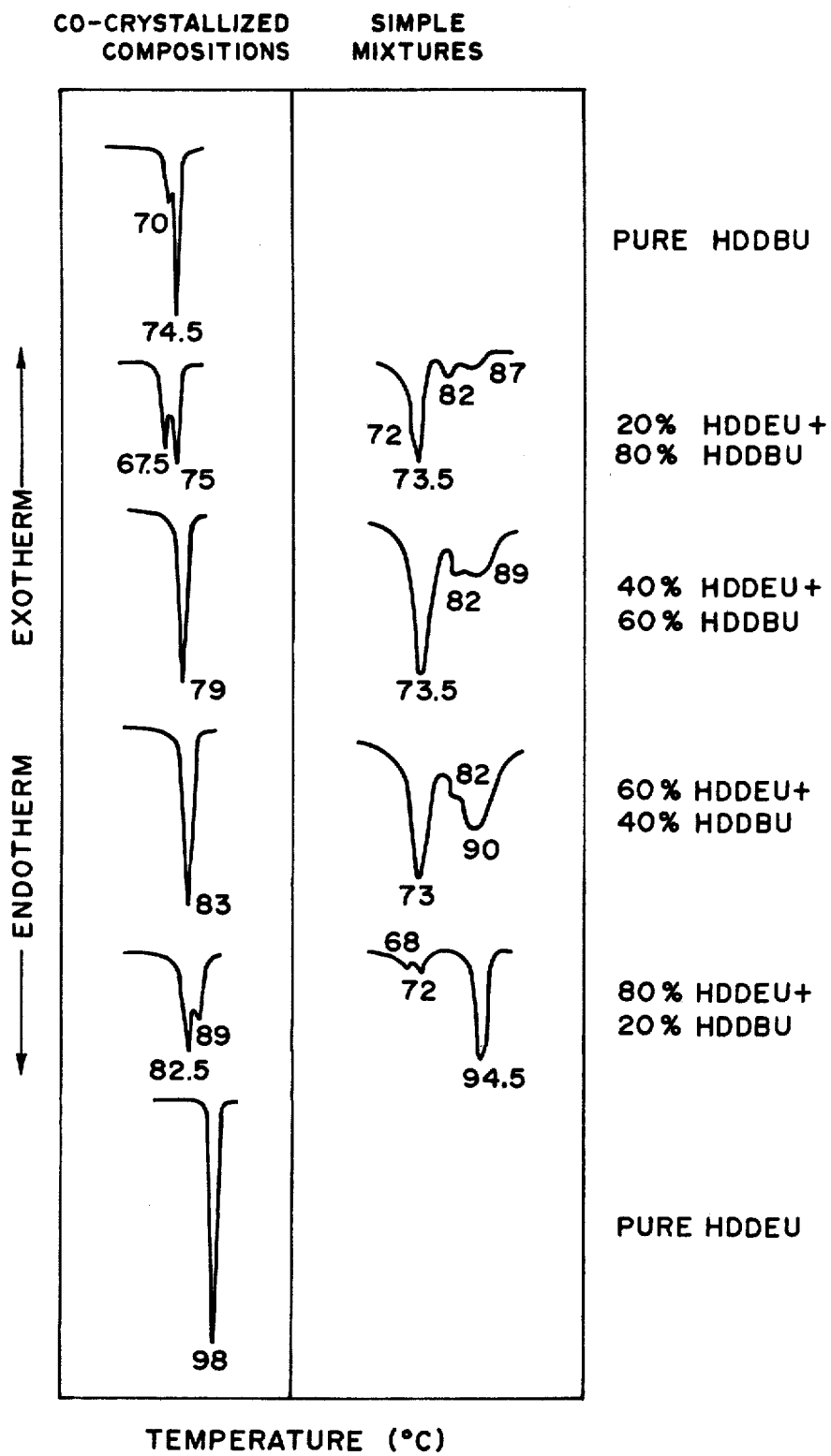
FIG. 2 illustrates thermograms, obtained by differential scanning calorimetry, of 2,4-hexadiyn-1,6-diol bis(n-butylurethane) (HDDBU) and 2,4-hexadiyn-1,6-diol bis(ethylurethane) (HDDEU), individually as pure materials and as co-crystallized compositions and simple mixtures thereof containing 20, 40, 60 and 80 weight percent of each component.

We have unexpectedly found that the thermal and radiation reactivity of acetylenic compounds containing at least one —C≡C—C≡C— group can be successfully altered by co-crystallizing two or more of the compounds, having different chemical structures, wherein the produced co-crystallized acetylenic compounds have either unexpectedly higher or lower reactivity upon exposure to actinic radiation or thermal annealing than the individual compounds. The term "actinic radiation" refers to ultraviolet radiation, gamma radiation, electron beam and the like which is of sufficiently high energy to cause chemical changes, i.e. polymerization by 1,4- addition between the acetylenic compounds. The term "thermal annealing" refers to heating at sufficient temperature, as by infrared radiation, flame, laser-beam, microwave radiation and the like which is sufficiently high energy to cause chemical changes, i.e. polymerization by 1,4- addition between the acetylenic compounds. By the term "co-crystallized" as used herein is meant a crystalline composition containing at least two different components in its crystalline lattice, wherein the new crystalline lattice exhibits different thermal properties and is distinguishable from the crystalline lattices of the individual components.

The co-crystallized compositions of acetylenic compounds of this invention are distinguishable and unique with respect to simple mixtures of the individual components in that the co-crystallized composition exhibits a substantially different thermogram than the sum of the thermograms of the individual components as measured by differential scanning calorimetry. This technique measures changes in enthalpy with respect to temperature over a broad temperature range and indicates melting behavior, phase changes and temperature of transitions. The thermogram of a simple mixture will, in general, exhibit the sum of the thermal behavior of the two components, whereas the co-crystallized composition will exhibit a substantially different thermogram.

By the term "substantially different thermogram" is meant that the thermogram of the co-crystallized composition will not be identical with respect to both the overall profile of endotherms and exotherms and the temperatures at which the endotherms and exotherms occur as contrasted to the thermogram of a simple mixture of the components. The differences will be readily distinguishable in that the thermogram of the co-crystallized composition will usually consist of one peak value while that of the simple mixture will usually consist of at least two distinct peak values, each corresponding to the peak value of each individual component. The thermogram of the co-crystallized composition will vary, depending upon the concentration of each of the components in the composition, wherein each component acetylenic compound is present in at least about 0.1 percent by weight of the composition. For example, an 80/20 composition by weight of 3,5-octadiyn-1,8-diol (ODD) and 4,6-decadiyn-1,10-diol (DDD) yields a single peak in the thermogram, whereas a 60/40 composition by weight of the same components yields a straight line, indicating the composition is amorphous and does not display crystalline characteristics in the temperature range usually measured, e.g. −100° C. to 200° C.

Since the co-crystallized composition exhibits a different thermogram, its crystalline properties are different from those of a simple mixture resulting in either greater or lesser polymerization reactivity and subsequent rate of color change upon exposure to actinic radiation or thermal annealing; whereas the simple mixture will exhibit properties which are merely an additive combination of the individual components depending upon the proportions of each component present. For example, a co-crystallized composition containing 12 weight percent 2,4-hexadiyn-1,6-diol bis(p-chlorophenylurethane) (HDDPCPU)/88 weight percent 2,4-hexadiyn-1,6-diol bisphenylurethane (HDDPU) exhibits an increased polymerization rate of about 700 times faster than that of a simple mixture of the two or 2,4-hexadiyn-1,6-diol bis(phenylurethane), alone.

Conversely, a co-crystallized composition of 2,4-hexadiyn-1,6-diol bis(p-toluenesulfonate) (HDDPTS) and 3,5-octadiyn-1,8-diol bis(p-toluenesulfonate (ODDPTS) exhibits a decreased reactivity toward polymerization by thermal annealing as contrasted to a simple mixture of the two.

This general altered reactivity of a co-crystallized composition is thought to be due to changes in the packing of the molecules in the solid state. Alteration of the crystallographic packing by the introduction of other closely related acetylenic molecules probably affects the activation energy or the kinetics of the polymerization process in an unexpected manner. Generally, the best results are obtained for achieving efficient crystallographic packing of the acetylenic molecules in the solid state if the molecules chosen have similar chemical structure. The thermal or radiation response which gives rise to the color changes of the co-crystallized composition usually corresponds to addition reactions which transform the conjugated acetylenic functionalities in the composition to fully conjugated chains of the type (=C—C≡C—C=)$_q$, where q corresponds to the number of mutually reacting acetylenic functionalities, which is dependent upon reaction conditions. The intense coloration of the polymerized compositions results from the fully conjugated chains.

The acetylenic compounds in the co-crystallized composition are of different chemical structures. Being different chemical structures, they may have the same empirical formulas, e.g. a composition comprised of the bis(p-chlorophenylurethane) and bis(o-chlorophenylurethane) of 2,4-hexadiyn-1,6-diol. However, the term "different chemical structures" does not include different molecular weight fractions of a polymer, such as

—[C≡C—(CH$_2$)$_2$OCONH(CH$_2$)$_6$NHOCO—(CH$_2$-)$_2$—C≡C]$_n$ where different values of n would give rise to different physical structures, having the same empirical formula, but not different chemical structures.

In general, any two acetylenic compounds, of different chemical structures, each containing at least one —C≡C—C≡C— group and substituents selected from the group consisting of sulfonate, urethane and alcohol radicals, wherein at least one of the acetylenic compounds is capable of undergoing a contrasting color change upon exposure to actinic radiation or thermal annealing, may be used to form the compositions of this invention.

Included among the suitable acetylenic compounds of the invention are diynes, triynes, tetraynes and hexaynes of the general formulas described in U.S. Pat. No. 3,999,946, wherein the acetylenic compounds contain substituents selected from the group consisting of sulfonate, urethane and alcohol radicals, wherein the substituents can be the same or different, and if different, result in an asymmetrically substituted acetylenic compound.

It is preferred in the invention to use the acetylenic compounds which are diynes and it is particularly preferred to use diynes selected from the group consisting of 2,4-hexadiyn-1,6-diol, 3,5-octadiyn-1,8-diol, 4,6-decadiyn-1,10-diol, 5,7-dodecadiyn-1,12-diol and urethane and sulfonate derivatives thereof.

Preferred urethane substituents include those of the formula RNHOCO— wherein R is C$_1$–C$_{18}$ alkyl, designated as containing 1 to 18 carbon atoms, and being linear or branched; C$_1$–C$_{14}$ alkoxycarbonylmethyl, that is, the alkyl portion of the radical containing 1 to 14 carbon atoms, and being linear or branched; phenyl; halophenyl, containing at least one halogen, such as fluorine, chlorine, bromine and iodine or mixtures thereof in the o, m and p-positions of the phenyl ring; C$_1$–C$_{14}$ alkylphenyl, designated as containing an alkyl group of 1 to 4 carbons being linear or branched, in the o, m, or p-positions of the phenyl ring; and C$_1$–C$_4$ alkoxyphenyl, that is, the alkyl portion of the radical containing 1 to 4 carbon atoms being either linear or branched in the o, m, or p-positions of the phenyl ring.

Representative examples of urethane substituents include those where R is methyl, ethyl, isopropyl, t-butyl, n-dodecyl and n-octadecyl; methoxy-, ethoxy-, isopropoxy-, t-butoxy, n-docecyloxy- and n-tetradecyloxycarbonylmethyl; p-chloro-, o-bromo-, m-iodo-, 2,4-dichloro-, 3,5-dibromo-, p-fluoro-, and 2-chloro-3-bromophenyl; o-tolyl-, m-tolyl-, p-tolyl, 4-ethyl-, 4-isopropyl-, 3-n-butyl- and 4-t-butylphenyl; p-methoxy-, o-ethoxy-, m-isopropoxy-, and p-t-butoxyphenyl.

Preferred sulfonate substituents include those of the formula ZSO$_2$O— wherein Z is C$_1$–C$_{18}$ alkyl, designated as containing 1 to 18 carbon atoms being linear or branched; phenyl; halophenyl, containing at least one halogen, such as fluorine, chlorine, bromine and iodine or mixtures thereof in the o, m or p-positions of the phenyl ring; C$_1$–C$_4$ alkylphenyl, designated as containing an alkyl group of 1 to 4 carbon atoms being linear or branched in the o, m or p-positions of the phenyl ring.

Representatives examples of sulfonate substituents include those where Z is methyl, ethyl, isopropyl, t-butyl, n-dodecyl and n-octadecyl; p-chloro-, o-bromo-, m-iodo-, 2,4-dichloro-, 3,5-dibromo-, p-fluoro-, and 2-chloro-3-bromophenyl; o-tolyl, m-tolyl, p-tolyl, 4-decylphenyl, 4-isopropylphenyl, 3-n-butylphenyl and 4-t-butylphenyl.

Examples of specific acetylenic compounds useful in the practice of the invention include:

A. Sulfonates 1. p—CH$_3$—C$_6$H$_4$SO$_3$CH$_2$—C≡C—C≡C—CH$_2$SO$_3$C$_6$H$_4$—p—CH$_3$
   2,4-hexadiyn-1,6-diol bis(p-toluenesulfonate)
2. p—CH$_3$—C$_6$H$_4$SO$_3$—(CH$_2$)$_2$—C≡C—C≡C—(CH$_2$)$_2$—SO$_3$—C$_6$H$_4$—p—CH$_3$
   3,5-octadiyn-1,8-diol bis(p-toluenesulfonate)

3. p—CH₃—C₆H₄SO₃CH₂—C≡C—C≡C—(CH₂-)₂—C≡CH 2,4,8-nonatriyn-1-ol p-toluene sulfonate 4. [p—CH₃—C₆H₄SO₃CH₂C≡C—C≡C—(CH₂-)₂—C≡C—]₂

2,4,8,10,14,16-octadecahexayn-1,18-diol bis(p-toluenesulfonate)

B. Urethanes

1. C₆H₅NHOCOCH₂—C≡C—C≡C—CH₂OCONHC₆H₅

2,4-hexadiyn-1,6-diol bis(phenylurethane)

2. C₂H₅NHOCOCH₂—C≡C—C≡C—CH₂OCONHC₂H₅

2,4-hexadiyn-1,6-diol bis(ethylurethane)

3. C₄H₉NHOCOCH₂—C≡C—C≡C—CH₂OCONHC₄H₉

2,4-hexadiyn-1,6-diol bis(n-butylurethane)

4. p—Cl—C₆H₄—NHOCOCH₂—C≡C—C≡C—CH₂OCONHC₆H₄—p—Cl 2,4-hexadiyn-1,6-diol bis(p-chlorophenylurethane)

5. p—Br—C₆H₄—NHOCOCH₂—C≡C—C≡C—CH₂OCONHC₆H₄—p—Br 2,4-hexadiyn-1,6-diol bis(p-bromophenylurethane)

6. C₆H₅(CH₂)₂C≡C—C≡C—CH₂OCONHC₂H₅

7-phenyl-2,4-heptadiyn-1ol-ethylurethane

7. C₂H₅NHOCO(CH₂)₂—C≡C—C≡C—(CH₂-)₂OCONHC₂H₅

3,5-octadiyn-1,8-diol bis(ethylurethane)

8. CH₃NHOCO(CH₂)₄—C≡C—C≡C—(CH₂-)₄OCONHCH₃

5,7-dodecadiyn-1,12-diol bis(methylurethane)

9. C₆H₅NHOCO(CH₂)₄—C≡C—C≡C—(CH₂-)₄OCONHC₆H₅

5,7-dodecadiyn-1,12-diol bis(phenylurethane)

10. CH₃NHOCOCH₂—C≡C—C≡C—(CH₂-)₂—C≡CH 2,4,8-nonatriyn-1-ol-methylurethane

11. C₂H₅NHOCOCH₂—C≡C—C≡C—(CH₂-)₂—C≡CH 2,4,8-nonatriyn-1-ol-ethylurethane

12. C₂H₅NHOCOCH₂—C≡C—C≡C—C≡C—C≡C—CH₂OCONHC₂H₅

2,4,6,8-decatetrayn-1,10-diol bis(ethylurethane)

13. CH₃NHOCO—CH₂—C≡C—C≡C—(CH₂-)₂—C≡C—C≡C—CH₂—OCONHCH₃

2,4,8,10-dodecatetrayn-1,12-diol bis(methylurethane)

14. C₂H₅NHOCOCH₂—C≡C—C≡C—(CH₂-)₂—C≡C—C≡C—CH₂OCONHC₂H₅

2,4,8,10-dodecatetrayn-1,12-diol bis(ethylurethane)

15. C₆H₅NHOCOCH₂—C≡C—C≡C—(CH₂-)₂—C≡C—C≡C—CH₂OCONHC₆H₅

2,4,8,10-dodecatetrayn-1,12-diol bis(phenylurethane)

16. [CH₃NHOCOCH₂—C≡C—C≡C—)₂—C≡C—]₂

2,4,8,10,14,16-octadecahexayn-1,18-diol bis(methylurethane)

17. [C₂H₅NHOCOCH₂—C≡C—C≡C—(CH₂-)₂—C≡C—]₂

2,4,8,10,14,16-octadecahexayn-1,18-diol bis(ethylurethane)

18. [C₆H₅NHOCOCH₂—C≡C—C≡C—(CH₂-)₂—C≡C—]₂

2,4,8,10,14,16-octadecahexayn-1,18-diol bis(phenylurethane)

C. Alcohols

1. HO—(CH₂)₂—C≡C—C≡C—(CH₂)₂—OH 3,5-octadiyn-1,8-diol

2. HO—(CH₂)₃—C≡C—C≡C—(CH₂)₃—OH 4,6-decadiyn-1,10-diol

3. HOOC(CH₂)₈—C≡C—C≡C—CH₂OH 10,12-tetradecadiynoic acid-14-ol

Similarly suitable for the practice of the invention are cyclic compositions such as

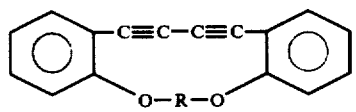

where R is —CO(CH₂)₃CO—, —CO(CH₂)₄CO—, —(CH₂)₃—, —CH₂CH CHCH₂—(cis or trans), —CH₂C CCH₂— or —CH₂(m—C₆H₄)CH₂—.

In general, any of the acetylenic compounds included in the invention can be mutually co-crystallized to form a co-crystallized composition. More than two acetylenic compounds can be employed with the provisos that at least one acetylenic compound undergoes a contrasting color change upon exposure to actinic radiation or thermal annealing, and each component is present in at least about 0.1 weight percent of the co-crystallized composition.

Representative examples of suitable co-crystallized compositions include the following:

Co-Crystallized Compositions 2,4-hexadiyn-1,6-diol bisphenylurethane and 2,4-hexadiyn-1,6-diol bis(p-bromophenylurethane)

2,4-hexadiyn-1,6-diol bisphenylurethane and 2,4-hexadiyn-1,6-diol bis(p-chlorophenylurethane)

3,5-octadiyn-1,8-diol; 4,6-decadiyn-1,10-diol 2,4-hexadiyn-1,6-diol bis(n-butylurethane) plus 2,4-hexdiyn-1,6-diol bis(ethylurethane)

2,4-hexdiyn-1,6-diol bis(p-bromophenylurethane)and 2,4-hexadiyn-1,6-diol bis(p-chlorophenylurethane)

2,4-hexadiyn-1,6-diol bis(p-chlorophenylurethane) and 2,4-hexadiyn-1,6-diol bis(p-chlorophenylurethane)

2,4-hexdiyn-1,6-diol bis(o-tolylurethane) plus 2,4-hexadiyn-1,6-diol bis(m-tolylurethane)

2,4-hexadiyn-1,6-diol bis(n-hexylurethane) plus 2,4-hexadiyn-1,6-diol bis(n-butylurethane)

2,4-hexadiyn-1,6-diol bis(m-tolylurethane) plus 2,4-hexadiyn-1,6-diol bis(p-tolylurethane)

2,4-hexadiyn-1,6-diol bis(o-tolylurethane) plus 2,4-hexadiyn-1,6-diol bis(p-tolylurethane)

2,4-hexadiyn-1,6-diol bis(m-chlorophenylurethane) plus 2,4-hexadiyn-1,6-diol bis(o-chlorophenylurethane)

2,4-hexadiyn-1,6-diol bis(p-tolylurethane) plus -hexadiyn-1,6-diol bis(p-chlorophenylurethane)

2,4-hexadiyn-1,6-diol bis(p-methoxyphenylurethane) plus 2,4-hexadiyn-1,6-diol bis(p-chlorophenylurethane)

2,4-hexadiyn-1,6-diol bis(phenylurethane) plus 2,4-hexadiyn-1,6-diol bis(m-chlorophenylurethane)

2,4-hexadiyn-1,6-diol bis(phenylurethane) plus 2,4-hexadiyn-1,6-diol bis(p-methoxyphenylurethane)

2,4-hexadiyn-1,6-diol bis(phenylurethane) plus 2,4-hexadiyn-1,6-diol bis(p-ethoxyphenylurethane)

2,4-hexadiyn-1,6-diol bis(phenylurethane) plus 2,4-hexadiyn-1,6-diol bis(o-chlorophenylurethane)

3,5-octadiyn-1,8-diol bis(p-chlorophenylurethane) plus 3,5-octadiyn-1,8-diol bis(m-chlorophenylurethane)

3,5-octadiyn-1,8-diol bis(m-tolylurethane) plus 3,5-octadiyn-1,8-diol bis(o-tolylurethane)

4,6-decadiyn-1,10-dio bis(n-butoxycarbonylmethylurethane) plus 4,6-decadiyn-1,10-diol bis(ethoxycarbonylmethylurethane)

5,7-dodecadiyn-1,12-diol bis(o-tolylurethane) plus 5,7-dodecadiyn-1,12-diol bis(m-tolylurethane)

5,7-dodecadiyn-1,12-diol bis(p-chlorophenylurethane) plus 5,7-dodecadiyn-1,12-diol bis(p-bromophenylurethane)

2,4-hexadiyn-1,16-diol bis(p-ethoxyphenylurethane) plus 3,5-octadiyn-1,8-diol bis(p-ethoxyphenylurethane)

2,4-hexadiyn-1,6-diol bis(m-tolylurethane) plus 3,5-octadiyn-1,8diol bis(m-tolylurethane)

2,4-hexadiyn-1,6-diol bis(n-hexylurethane) plus 3,5-octadiyn-1,8-diol bis(n-hexylurethane)

2,4-hexadiyn-1,6-diol bis(m-chlorophenylurethane) plus 3,5- octadiyn-1,8-diol bis(m-chlorophenylurethane)

2,4-hexadiyn-1,6-diol bis(n-butylurethane) plus 5,7-dodecadiyn-1,12-diol bis(n-butylurethane)

4,6-decadiyn-1,10-diol bis(n-butylurethane) plus 5,7-dodecadiyn- 1,12-diol bis(n-butylurethane)

3,5- octadiyn-1,8-diol plus 4,6-decadiyn-1,10-diol 2,4-hexadiyn-1,6-diol bis(p-ethoxyphenylurethane) plus 2,4-hexadiyn-1,6-dio bis(phenylurethane)

2,4-hexadiyn-1,6-diol bis(p-tolylurethane) plus 2,4-hexadiyn-1,6diol bis(p-chlorophenylurethane)

2,4-hexadiyn-1,6-diol bis(p- methoxyphenylurethane) plus 2,4-hexadiyn- 1,6-diol bis(p-chlorophenylurethane 2,4-hexadiyn-1,6-diol bis(o-chlorophenyl)urethane plus 2,4-hexadiyn-1,6-diol bisphenylurethane Preferred co-crystallized compositions are: 2,4-hexadiyn-1,6-diol bis(phenylurethane) and 2,4-hexadiyn-1,6-diol bis(p-bromophenylurethane); 2,4-hexadiyn-1,6-diol bis(phenylurethane) and 2,4-hexadiyn-1,6diol bis(p-chlorophenylurethane); 2,4-hexadiyn-1,6-diol bis(n-butylurethane and 2,4-hexadiyn-1,6-diol bis(ethylurethane); 2,4-hexadiyn-1,6-diol bis(p-toluenesulfonate) and 3,5-octadiyn-1,8-diol bis(p-toluenesulfonate); and 3,5-octadiyn-1,8-diol and 4,6-decadiyn-1,10-diol.

Particularly preferred are the compositions containing 2,4-hexadiyn-1,6-diol bis(phenylurethane) and 2,4-hexadiyn-1,6-diol bis(p-chlorophenylurethane) or 2,4-hexadiyn-1,6-diol bis(p-bromophenylurethane) wherein each of the latter two components are present from about 0.1 to about 30 weight percent of the composition.

In general, the co-crystallized composition of this invention will gradually undergo a color change, upon thermal annealing or exposure to actinic radiation, from colorless to a red color and finally to a dark metallic color. In certain instances, the color change may be other than through a gradual red transition, for example, a blue transition, and the final color may be a dark blue but not necessarily metallic. However, in either event, the co-crystallized composition is useful in the applications described herein.

Certain co-crystallized compositions are unexpectedly thermochromic; that is, upon thermal annealing or exposure to actinic radiation they gradually form a dark or metallic color and then upon further thermal annealing they turn deep red, but in a reversible fashion, over a narrow range of temperature. If coated on the surface of an article or suitable substrate, these thermochromic compositions will exhibit this reversible contrasting color change when a definite temperature is reached and thus can be used to indicate a specific temperature. The temperature of the reversible color transition can be varied by suitable adjustment of the proportions of the individual acetylenic compounds producing different co-crystallized compositions which can be used to cover a wide range of temperatures just like a thermometer.

Examples of co-crystallized compositions which are thermochromic are 4,6-decadiyn-1,10-diol bis(ethoxycarbonylmethylurethane) and 4,6-decadiyn-1,10-diol bis(n-butoxycarbonylmethylurethane); and 4,6-decadiyn-1,10-diol bis(ethoxycarbonylmethylurethane) and 5,7-dodecadiyn-1,12-diol bis(ethoxycarbonylmethylurethane).

Figure 3:
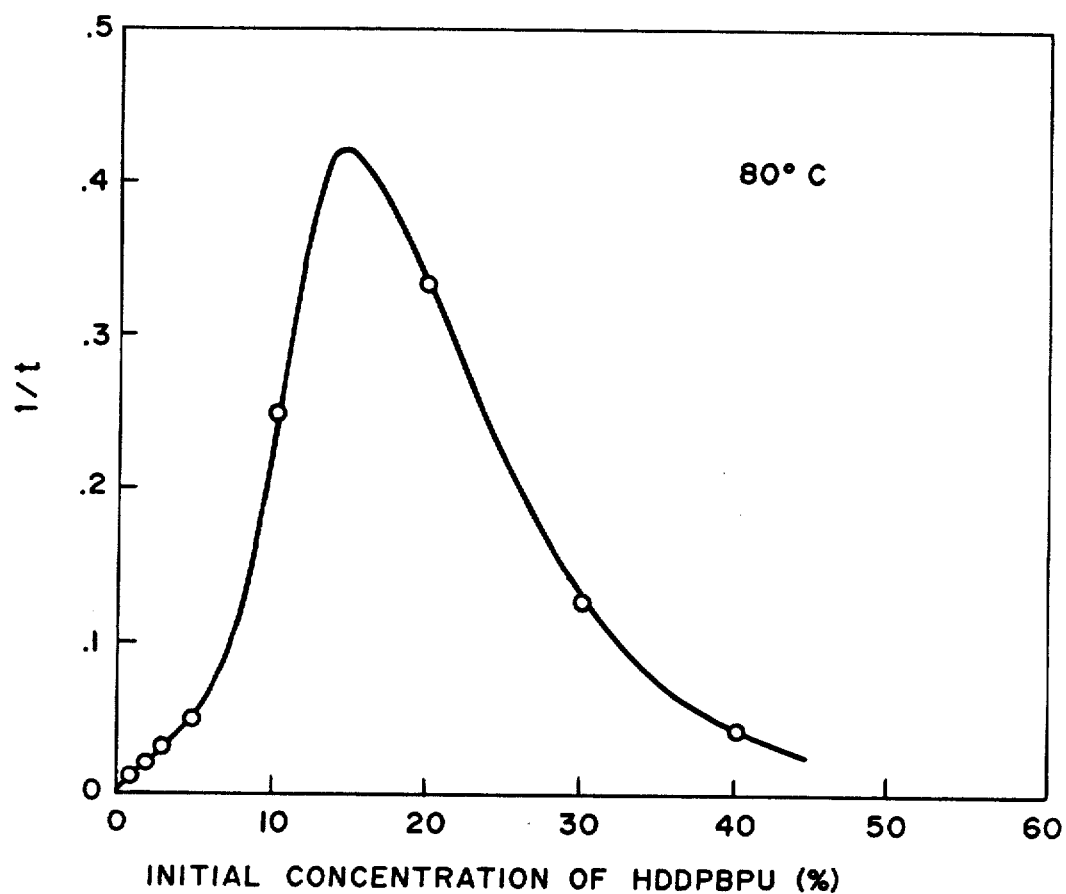
FIG. 3 illustrates a plot of reciprocal time in hours (ordinate) versus the initial concentration in the composition, prior to thermal annealing, of 2,4-hexadiyn-1,6-diol bis(bromophenylurethane) (HDDPBPU) as weight percent in co-crystallized compositions of HDDPBPU and 2,4-hexadiyn-1,6-diol bisphenylurethane (HDDPU) indicating the relationship of time required for the co-crystallized composition to turn metallic green or rusty red (end point color) by thermal annealing at 80° C., as a function of the concentration of HDDPBPU in the co-crystallized composition. The extrapolated portion of the curve between 10 and 20 weight percent concentration of HDDPBPU is an approximate fit of the experimental points from FIG. 4 and represents the region of optimum thermal reactivity of these co-crystallized compositions.

Certain co-crystallized compositions exhibit a novel property in that the thermal reactivity, i.e. the rate of color development upon thermal annealing, is greater than any of the component acetylenic compounds. For example, co-crystallized compositions of HDDPU, 2,4-hexadiyn-1,6-diol bis (phenylurethane) and HDDPCPU, 2,4-hexadiyn-1,6-dio bis p-chlorophenylurethane); and, HDDPU and HDDPBPU, 2,4-hexadiyn-1,6-diol bis(p-bromophenylurethane) exhibit thermal reactivity rates which are greater by a factor of at least about two and usually above ten, than either of the reactivities of the individual acetylenic compounds. FIG. 3 illustrates that the thermal reactivity of HDDPU/HDDPBPU co-crystallized compositions are greater than the thermal reactivity of HDDPU, which has about the same thermal reactivity as HDDPBPU. Co-crystallized compositions which exhibit a greater thermal reactivity than any of the component acetylenic compounds are also a subject of this invention and include co-crystallized compositions of HDDPU/HDDPCPU; HDDPU/HDDPBPU; and HDDEU, 2,4-hexadiyn-1,6-diol bis (ethylurethane)/HDDBU, 2,4-hexadiyn-1,6-diol bis(n-butylurethane).

Five processes for making the co-crystallized compositions of the invention from the acetylenic compounds described herein are also subjects of this invention. The first process comprises the steps of (a) dissolving at least two acetylenic compounds in a solvent therefor, thereby forming a solution; (b) recovering the co-crystallized composition from the solution by removal of the solvent at such rate that it exceeds the rate of initiating crystallization of each acetylenic compound separately.

The fast rate of removal of the solvent can be accomplished by distillation of the solvent under reduced pressure or by rapid spray drying of the solution. In either modification, the solvent is removed at a faster rate than the rate of initiating crystallization of each acetylenic compound separately, which thereby results in a co-crystallized composition since now the acetylenic compounds will uniformly co-crystallize out of the solution at the same rate. It is preferred to use spray drying as the technique for evaporating the solvent since it doesn't require the use of bulky vacuum distillation equipment.

One modification of this process is to deposit the solution as by spray drying directly onto a substrate in step (a) of the above process, thereby resulting in a co-crystallized composition being directly applied to a substrate for use as a time-temperature or radiation-dosage indicator.

Suitable solvents for the process include alkyl esters of monocarboxylic acids, higher alkyl alcohols containing more than one carbon atom, alkylated benzenes, cyclic ethers, alkyl ketones, alkyl glycol ethers, halogenated alkyl hydrocarbons and the like. Representative examples include ethyl acetate, methyl propionate, ethanol, butanol, isopropanol, toluene, xylene, trimethylbenzene, isopropylether, 1,2-dimethoxyethane, tetrahydrofuran, dioxane, acetone, ethylmethyl ketone, chloroform, dichloromethane and mixtures thereof. Especially preferred as solvents are 1,2-dimethoxyethane, dioxane, tetrahydrofuran, acetone, chloroform, ethanol, xylene and ethyl acetate. The process may be conducted, for example, at room temperature by rapid evaporation of solutions containing from about 0.0001 to 5.0 parts, and preferably about 0.002 to 0.2, parts by weight of combined acetylenic compounds per part by weight of solvent or solvent blend.

The second process comprises the steps of (a) dissolving at least two acetylenic compounds in a solvent therefor, thereby forming a solution; (b) mixing the solution with a liquid, which is miscible with the solvent, but is a non-solvent for the co-crystallized composition, at such rate that mixing is complete before the initiation time for crystallization of each acetylenic compound separately from the same solvent mixture.

The solvents which are applicable in this process are the same as those discussed above.

Suitable liquids which are miscible with the solution solvent but act as a non-solvent for the composition include paraffins, such as hexane and heptane, lower alkyl ethers containing 2 to 4 carbon atoms, such as diethyl ether, water, methanol and benzene.

The weight ratio of solvent to total weight of acetylenic compounds is the same as described above and generally the weight ratio of liquid to solvent is about 1 to 10 parts of lqiuid per part of solvent and it is preferred to use about 5 parts of liquid per part of solvent.

Mixing can be accomplished by either adding the solution of acetylenic compounds to the liquid or by vice versa. However, it is preferred to add the solution to the liquid with adequate stirring to insure complete conversion of the acetylenic compounds to a co-crystallized composition. In general, mixing is carried out at ambient temperature.

The third process comprises synthesizing the co-crystallized compositions directly in the solvent which comprises the steps of: (a) reacting one or more acetylenic diols with one or more isocyanates or organic sulfonyl acid agents, such that the total of different diols and isocyanates or organic sulfonic acid agents is at least three; and (b) recovering the co-crystallized composition from the solution.

The solvents useful in this process are the same as described above.

The acetylenic diols, isocyanates and organic sulfonic acid reagents suitable in the process are adequately described both in U.S. Pat. No. 3,999,946 and in the above discussion, where the isocyanates contain R radicals including those discussed previously and the organic sulfonic acid agents contain Z radicals including those discussed previously. The acetylenic diols, isocyanates and organic sulfonic acid reagents and combinations thereof will become obvious to one skilled in the art from a reading of the above patent and the above disclosure contained herein.

The limitation in this process is that the total number of diols and isocyanates or diols and organic sulfonic acid agents is at least three, thereby resulting in a co-crystallized composition directly recoverable from the reaction mixture. For example, methylisocyanate can be reacted with a mixture of 2,4-hexadiyn-1,6-diol and 3,5-oxtadiyne-1,8-diol to yield a co-crystallized composition of (1) 2,4-hexadiyn-1,6-diol bis(methylurethane) and (2) 3,5-octadiyn-1,8-diol bis(methylurethane). Similarly, methylisocyanate and ethylisocyanate can be reacted with 2,4-hexadiyn-1,6-diol to yield a co-crystallized composition of (1) 2,4-hexadiyn-1,6-diol bis(methylurethane), (2) 2,4-hexadiyn-1,6-diol bis(ethylurethane) and (3) 2,4-hexadiyn-1-ol-methylurethane-6-ol-ethylurethane.

It is preferred in the process to react one acetylenic diol with at least two isocyanates or at least two organic sulfonic acid agents.

The fourth process for preparing co-crystallized compositions of this invention comprises (a) forming a melt of at least two acetylenic compounds and (b) cooling the melt rapidly.

In general, two or more acetylenic compounds are mixed and heated above their melting points, or until a melt is formed and upon rapidly cooling a co-crystallized composition is obtained. By the term "rapid cooling" is meant cooling at a faster rate than the rate of initiating crystallization of each acetylenic compound separately. Deposition of a mixture of acetylenic compounds from solution resulting in a finely divided mixture, followed by heating until a melt is formed, then rapidly cooling, is a preferred method of obtaining a co-crystallized composition from the melt. For example, the co-crystallized compositions of ODD/DDD, whose thermograms are illustrated in FIG. 1, were prepared by deposition of a mixture of the two compounds from acetone solution, and subsequent heating until a melt formed followed by rapid cooling. Alternately, if the temperature of the solution is above that of the melting points of the individual acetylenic compounds, evaporation of the solution will lead directly to a melt.

A fifth process for preparing co-crystallized compounds of this invention comprises (a) vaporizing at least two acetylenic compounds and (b) depositing the resulting vapor onto a substrate.

In the vapor form, a mixture of the aceylenic compounds will be formed, which upon deposition will result in a co-crystallized composition. Converting the acetylenic compounds into the vapor form can be accomplished in a number of conventional ways, but it is preferred to sublime the acetylenic compounds under reduced pressure by heating. Suitable substrates are discussed above for the deposition.

Devices for measuring temperature, comprising thermochromic co-crystallized compositions of this invention, and devices for measuring time-temperature and radiation-dosage history comprising co-crystallized compositions can be utilized for commercial articles.

A device for measuring temperature is also a subject of the invention comprising a substrate having deposited thereon at least one thermochromic co-crystallized composition of this invention. A thermochromic co-crystallized composition can be selected exhibiting a contrasting color change in the temperature region of interest and will reproducibly exhibit this color change through many heating and cooling cycles. Any suitable substrates may be chosen such as cardboard, filter paper, flexible polymers, such as polyethylene, polypropylene and the like, which choice will be obvious to one skilled in the art for a suitable application.

Further provided is a device comprising a series of thermochromic co-crystallized compositions, deposited on a substrate, each of which has a progressively higher thermochromic transition temperature than the prior composition in the series.

A device for measuring time-temperature or radiation-dosage history of an article is also a subject of this invention and comprises a substrate having deposited thereon a co-crystallized composition of this invention which undergoes an irreversible color change upon exposure to thermal annealing or radiation, in which the hue and intensity of developed color are an integrated history of such exposure which can be determined by reference to a suitable standard.

A specific embodiment of the device for measuring time-temperature or irradiation-dosage history of an article comprises a series of co-crystallized acetylenic compounds in which the reactivity, i.e. the rate of color development, the rate of undergoing a contracting color change, upon thermal annealing or exposing to actinic radiation, of each composition in the series is greater to a known extent than the prior composition in the series. Thus, upon thermal annealing or exposing to actinic radiation, an integrated time-temperature or radiation-dosage history of the exposure time will be represented by the developed colors of the individual compositions. The difference in reactivity of each co-crystallized composition is achieved by varying the weight ratio of the composite acetylenic compounds comprising the composition. FIG. 4 illustrates a general device of this type wherein a series of co-crystallized compositions containing different weight ratios of HDDPU/HDDPBPU exhibit different rates of color development upon thermal annealing at 80° C.

Commercial articles are stored in different types of containers such as metal cans, glass bottles, plastic bags or bottles and paper or cardboard bags or boxes. The co-crystallized compositions of this invention as thermometer devices or time-temperature or radiation-dosage devices can either be coated directly on the containers or can be coated on paper or plastic and then applied, such as by pressure tape, to the containers. In either case a binder to bind the crystals of the co-crystallized compositions to the containers is required. In the present case we have used either shellac commonly available such as that made by Park Corporation, Somerset, Massachusetts, or lacquer such as that made by Zynoltye Products Company, Compton, California or a binder. In some examples no binder was used and the co-crystallized compositions were coated directly on a substrate. Whatman filter papers (1) and aluminum foils (2 to 10 mils thick) have been used as substrates. The co-crystallized compositions were coated from solution either by spraying, spreading or brushing solution on a substrate. The compositions can also be coated by dipping the substrate in the solution. Coating experiments can be easily used to obtain uniform coatings of the co-crystallized compositions on a substrate.

Also a subject of this invention is a copolymeric composition comprising an irradiated or thermally annealed product of a composition comprised of at least two acetylenic compounds, each containing at least one —C≡C—C≡C— groups, and substituents selected from the group consisting of sulfonate, urethane and alcohol radicals, at least one of the compounds capable of undergoing a contrasting color change upon exposure to actinic radiation or thermal annealing, wherein the co-crystallized composition exhibits a substantially different thermogram than the sum of the individual components as obtained by differential scanning calorimetry.

Included among the copolymeric compositions are the co-crystallized compositions of this invention which have been thermally annealed or exposed to actinic radiation, such as gamma radiation, to form a copolymer which is useful in many polymer applications.

A specific embodiment of the copolymeric compositions is a shaped article, including a molded film, made from the copolymeric composition, wherein the decomposition temperature of the copolymeric composition is at least about 20° C. above the melting point of the composition.

This limitation is necessary to avoid degradation or charring of the copolymeric composition upon compression or extrusion molding above its melting point under pressure. In general, the molding process is usually conducted at a temperature up to about 20° C. above the melting point, wherein no degradation of the copolymer occurs that would adversely affect quality of the molded product.

For example, the melting point of a copolymeric composition of 80/20 weight percent of DDDEC-MU/4DECMU, i.e., 4,6-decadiyn-1,10-diol bis(ethoxycarbonylmethylurethane)/5,7-dodecadiyn-1,12-diol bis(ethoxycarbonylmethylurethane) produced by irradiating the co-crystallized composition with 50 Mrads, is 185°-195° C., and the decomposition temperature is 230°-260° C., thus allowing the copolymeric composition to be heat molded into shaped articles, including molded films.

Representative examples of copolymeric compositions which can be melted and shaped into articles or molded into films include 80/20 and 50/50 weight percent compositions of DDDECMU/4DECMU, and 50/50 and 20/80 weight percent compositions of DDDECMU/DDDBCMU, where DDDBCMU is 4,6-decadiyn-1,10-diol bis(n-butoxycarbonylmethylurethane). Other representative examples are listed in Table VIII of Example 43.

In general, the copolymeric compositions are prepared by thermal annealing or irradiating a co-crystallized composition of this invention, with actinic radiation, preferably gamma radiation of a dosage of about 50 Mrads and then treating with solvent to extract unreacted monomer. The copolymeric composition is then subjected to conventional molding techniques to produce a shaped article, preferably a molded film, which is useful in packaging and protective surface applications.

Thermal Reactivity

EXAMPLE 1

This example illustrates an increase in thermal reactivity by co-crystallization of 2,4-hexadiyn-1,6 bis(phenylurethane) (HDDPU) and 2,4-hexadiyn-1,6-diol bis(p-bromophenylurethane) (HDDPBPU).

Table 1 lists solutions of HDDPU and HDDPBPU which were prepared in 20 ml. of acetone with 4 ml of lacquer added as a binder:

TABLE I

| Solution No. | Weight of HDDPU, g. | Weight of HDDPBPU, g. |
|---|---|---|
| 1 | 2 | — |
| 2 | 1.99 | 0.01 |
| 3 | 1.98 | 0.02 |
| 4 | 1.96 | 0.04 |
| 5 | 1.94 | 0.06 |
| 6 | 1.90 | 0.10 |
| 7 | 1.80 | 0.20 |
| 8 | 1.60 | 0.40 |
| 9 | 1.40 | 0.60 |
| 10 | 1.20 | 0.80 |

Each solution was then sprayed over a Whatman filter paper number 1 (9 inch by 9 inch). The filter papers were first dried by dry nitrogen flow and then under vacuum. The drying process took about three minutes. The filter papers were then cut into 1 square inch pieces and stored at −20° C. The pieces of the filter paper were annealed at 80° C. for different periods of time. After annealing, the filter paper pieces were mounted according to their annealing time and concentration (proportion) of HDDPU to form an array as depicted in FIG. 4. A graph is shown in FIG. 3 for an annealing temperature of 80° C., in which the required time to turn metallic (end-point) in reciprocal hours is plotted versus concentration of HDDPBPU in the composition. It is apparent from the FIG. 3 that the thermal reactivity of HDDPU is increased by co-crystallizing with HDDPBPU. The reactivity is maximum between 10 and 20 percent of HDDPBPU, and the same effect was observed with co-crystallized compositions of HDDPU and 2,4-hexadiyn-1,6-diol bis(p-chlorophenylurethane) (HDDPCPU).

EXAMPLE 2

This example illustrates a decrease in thermal reactivity by co-crystallization of 2,4-hexadiyn-1,6-diol bis(p-toluenesulfonate) (HDDPTS), and 3,5-oxtadiyn-1,8-diol bis(p-toluenesulfonate) (ODDPTS), for use in time-temperature indicators.

HDDPTS is thermally polymerizable while ODDPTS is not. Table II lists compositions of HDDPTS and ODDPTS were prepared in 12 ml of chloroform plus 3 ml of acetone; 3 ml of lacquer was added to each solution as a binder: 100% by weight of HDDPTS; 9:1 by weight of HDDPTS/ODDPTS; 8:2 by weight of HDDPTS/ODDPTS; and 7:3 by weight of HDDPTS/ODDPTS.

TABLE II

Approximate Time (hrs) Required to Turn Metallic at Different Relative Temperatures

| Composition | Temperature | | | | |
|---|---|---|---|---|---|
| | 40° C. | 50° C. | 60° C. | 70° C. | 80° C. |
| 100% HDDPTS | 265 | 89 | 25 | 15 | 10 |
| 9:1 HDDPTS/ODDPTS | 400 | 114 | 35 | 20 | 10 |
| 8:2 HDDPTS/ODDPTS | — | 265 | 64 | 25 | 10 |
| 7:3 HDDPTS/ODDPTS | — | 400 | 89 | 50 | — |

Each solution was sprayed over an aluminum foil (9 inch by 9 inch). The coating was first dried by dry nitrogen and then under vacuum. The foil was then cut into 1 square inch pieces and annealed at approximately 40°, 50°, 60°, 70° and 80° C. for 1, 2, 5, 10, 15, 25, 35, 45, 64, 89, 114, 139, 164, 216, 265 and 400 hrs. The annealed pieces were then mounted on sticky paper according to time and temperature for each concentration. The time required for the co-crystallized acetylenic compounds to go metallic from red was estimated and the data are tabulated in the above Table. As can be seen from the Table, for a given relative temperature, the time required for the co-crystallized acetylenic compounds to go metallic increased with increasing concentration of ODDPTS. The estimated time required for HDDPTS alone to go metallic from red was about 3 to 4 months at room temperature (25° C.). Upon co-crystallization of HDDPTS with ODDPTS (30 percent by weight) the time required for the co-crystallized material to go metallic at room temperature was increased to about 12 to 15 months.

EXAMPLES 3–29: Co-crystallized Acetylenic Compounds

The following pairs of acetylenic compounds were co-crystallized and tested and found useful as time-temperature indicators:

| Example No. | Pairs of Co-crystallized Acetylenic Compounds |
|---|---|
| 3 | 2,4-hexadiyn-1,6-diol bis(n-butylurethane) plus 2,4-hexadiyn-1,6-diol bis(ethylurethane) |
| 4 | 2,4-hexadiyn-1,6-diol bis(p-bromophenylurethane) and 2,4-hexadiyn-1,6-diol bis(p-chlorophenylurethane) |
| 5 | 2,4-hexadiyn-1,6-diol bis(p-chlorophenylurethane) plus 2,4-hexadiyn-1,6-diol bis(o-chlorophenylurethane |
| 6 | 2,4-hexadiyn-1,6-diol bis(p-methoxyphenylurethane) plus 2,4-hexadiyn-1,6-diol bis(m-methoxyphenylurethane) |
| 7 | 2,4-hexadiyn-1,6-diol bis(o-tolylurethane) plus 2,4-hexadiyn-1,6-diol bis(m-tolylurethane) |
| 8 | 2,4-hexadiyn-1,6-diol bis(n-hexylurethane) plus 2,4-hexadiyn-1,6-diol bis(n-butylurethane) |
| 9 | 2,4-hexadiyn-1,6-diol bis(m-tolylurethane) plus 2,4-hexadiyn-1,6-diol bis(p-tolylurethane) |
| 10 | 2,4-hexadiyn-1,6-diol bis(o-tolylurethane) plus 2,4-hexadiyn-1,6-diol bis(p-tolylurethane) |
| 11 | 2,4-hexadiyn-1,6-diol bis(m-chlorophenylurethane) plus 2,4-hexadiyn-1,6-diol bis(o-chlorophenylurethane) |
| 12 | 2,4-hexadiyn-1,6-diol bis(p-tolylurethane) plus 2,4-hexadiyn-1,6-diol bis(p-chlorophenylurethane) |
| 13 | 2,4-hexadiyn-1,6-diol bis(p-methoxyphenylurethane) plus 2,4-hexadiyn-1,6-diol bis(p-chlorophenylurethane) |
| 14 | 2,4-hexadiyn-1,6-diol bis(phenylurethane) plus 2,4-hexadiyn-1,6-diol bis(m-chlorophenylurethane) |
| 15 | 2,4-hexadiyn-1,6-diol bis(phenylurethane) plus 2,4-hexadiyn-1,6-diol bis(p-methoxyphenylurethane) |
| 16 | 2,4-hexadiyn-1,6-diol bis(phenylurethane) plus 2,4-hexadiyn-1,6-diol bis(p-ethoxyphenylurethane) |
| 17 | 2,4-hexadiyn-1,6-diol bis(phenylurethane) plus 2,4-hexadiyn-1,6-diol bis(o-chlorophenylurethane) |
| 18 | 3,5-octadiyn-1,8-diol bis(p-chlorophenylurethane) plus 3,5-octadiyn-1,8-diol bis(m-chlorophenylurethane) |
| 19 | 3,5-octadiyn-1,8-diol bis(m-tolylurethane) plus 3,5-ocatdiyn-1,8-diol bis(o-tolylurethane) |
| 20 | 4,6-decadiyn-1,10-diol bis(butoxycarbonylmethylurethane) plus 4,6-decadiyn-1,10-diol bis(ethoxycarbonylmethylurethane) |
| 21 | 5,7-dodecadiyn-1,12-diol bis(o-tolylurethane) plus 5,7-dodecadiyn-1,12-diol bis(m-tolylurethane) |
| 22 | 5,7-dodecadiyn-1,12-diol bis(p-chlorophenylurethane) |

| Example No. | Pairs of Co-crystallized Acetylenic Compounds |
|---|---|
| | plus 5,7-dodecadiyn-1,12-diol bis(p-bromophenyl-urethane) |
| 23 | 2,4-hexadiyn-1,6-diol bis(p-ethoxyphenylurethane) plus 3,5-octadiyn-1,8-diol bis(p-ethoxyphenyl-urethane) |
| 24 | 2,4-hexadiyn-1,6-diol bis(m-tolylurethane) plus 3,5-octadiyn-1,8-diol bis(m-tolylurethane) |
| 25 | 2,4-hexadiyn-1,6-diol bis(n-hexylurethane) plus 3,5-octadiyn-1,8-diol bis(n-hexylurethane) |
| 26 | 2,4-hexadiyn-1,6-diol bis(m-chlorophenylurethane) plus 3,5-octadiyn-1,8-diol bis(m-chlorophenyl-urethane) |
| 27 | 2,4-hexadiyn-1,6-diol bis(n-butylurethane) plus 5,7-dodecadiyn-1,12-diol bis(n-butylurethane) |
| 28 | 4,6-decadiyn-1,10-diol bis(n-butylurethane) plus 5,7-dodecadiyn-1,12-diol bis(n-butylurethane) |
| 29 | 3,5-octadiyn-1,6-diol plus 4,6-decadiyn-1,10-diol |

EXAMPLE 30

Some acetylenic compounds which upon co-crystallization do not show any thermal reactivity (or very little thermal reactivity) are still polymerizable by high energy radiation and can be used as radiation dosage indicators. The following are examples.

Co-crystallization of 2,4-hexadiyn-1,6-diol bis(m-chlorophenylurethane) (HDDMCPU) and 2,4-hexadiyn-1,6-diol bis(phenylurethane) (HDDPU) for use as radiation dosage indicators.

TABLE III lists solutions of HDDMCPU and HDDPU which were prepared in 10 ml of tetrahydrofuran; 2 ml of commercial shellac was added as a binder.

TABLE III

| Weight of HDDMCPU, g. | Weight of HDDPU, g. |
|---|---|
| 1.0 | — |
| 0.9 | 0.1 |
| 0.8 | 0.2 |
| 0.7 | 0.3 |
| 0.6 | 0.4 |
| 0.5 | 0.5 |
| 0.4 | 0.6 |
| 0.3 | 0.7 |
| 0.2 | 0.8 |
| 0.1 | 0.9 |
| — | 1.0 |

Each solution was sprayed on a 6 inch by 6 inch square of aluminum foil. The coating was dried under a stream of nitrogen followed by vacuum-drying for 24 hrs. The co-crystallized HDDMCPU and HDDPU were not thermally polymerizable prior to irradiation. The squares of aluminum foil were then cut into 1 inch by 1 inch pieces and irradiated with Co$^{60}$γ-rays at room temperature in air for dosages of 1, 2, 3, 4, 5, 6, 7, 8, 9 and 10 Mrads. The dose required for the co-crystallized acetylenic compounds turn to dark (dark violet) is shown in the following Table IV.

TABLE IV

| Proportion of HDDMCPU, % | Dose Required to go Dark, Mrads | Comment |
|---|---|---|
| 100 | 7–8 | — |
| 90 | 3 | — |
| 80 | 2 | — |
| 70 | — | unreactive (pale yellow color) |
| 60 | — | unreactive (pale yellow color) |

TABLE IV-continued

| Proportion of HDDMCPU, % | Dose Required to go Dark, Mrads | Comment |
|---|---|---|
| 50 | 4 | — |
| 40 | less than 1 | turns almost black |
| 30 | 2 | — |
| 20 | 4 | — |
| 10 | 2 | — |
| 0 | 3 | — |

Example 31

Co-crystallization of 2,4-hexadiyn-1,6-diol bis(phenylurethane) (HDDPU) and 3,5-octadiyn-1,8-diol bis(phenylurethane) (ODDPU) for use as radiation dosage indicators.

Table V lists solutions of HDDPU and ODDPU which were prepared in 10 ml of tetrahydrofuran; 2 ml of commercial lacquer was added as a binder. Each solution was sprayed on a 6 inch by 6 inch square of Number 1 Whatman filter paper was preprinted with numerals 111—, 222—, and the like.

TABLE V

| Weight of HDDPU, g. | Weight of ODDPU, g. |
|---|---|
| 1.0 | — |
| 0.9 | 0.1 |
| 0.7 | 0.3 |
| 0.5 | 0.5 |
| 0.3 | 0.7 |
| 0.1 | 0.9 |
| — | 1.0 |

The coating was dried under a nitrogen flow followed by vacuum-drying for 25 hrs at room temperature. The co-crystallized acetylenic compounds were not thermally polymerizable prior to radiation, that is, they did not show any coloration even after a month at room temperature. The filter paper was cut into narrow strips, each having a specific number which was clearly visible after coating. The strips were then irradiated with Co$^{60}$γ-rays at room temperature in air for dosages of 1, 2, 3, 4, 5, 6, 7, 8, 9 and 10 Mrads. Upon irradiation the coating turned pink-red or dark violet in color. The dose required for the number printed underneath to become invisible is shown in the following table.

TABLE VI

| Percent of HDDPU | Dose, Mrads Required for the Number to Become Invisible |
|---|---|
| 100 | less than 1 |
| 90 | 4 |
| 70 | 1–2 |
| 50 | 1 |
| 30 | 4 |
| 10 | 1–2 |
| 0 | 2 |

The results indicate that co-crystallized compositions containing 90 and 30 weight percent HDDPU exhibit highly desirable radiation-dosage characteristics since they are able to measure a larger amount of gamma radiation.

Examples 32 to 36

The following is a list of pairs of acetylenic compounds which were co-crystallized and tested as radiation dosage indicators. The method of study used in the following examples was the same as in Example 30.

| Example | Co-crystallized Pairs |
|---|---|
| 32 | 2,4-hexadiyn-1,6-diol bis(m-chlorophenylurethane), and 2,4-hexadiyn-1,6-diol bis(phenylurethane) |
| 33 | 2,4-hexadiyn-1,6-diol bis(p-ethoxyphenylurethane) plus 2,4-hexadiyn-1,6-diol bis(phenylurethane) |
| 34 | 2,4-hexadiyn-1,6-diol bis(p-tolylurethane) plus 2,4-hexadiyn-1,6-diol bis(p-chlorophenylurethane) |
| 35 | 2,4-hexadiyn-1,6-diol bis(p-methoxyphenylurethane) plus 2,4-hexadiyn-1,6-diol bis(p-chlorophenylurethane) |
| 36 | 2,4-hexadiyn-1,6-diol bis(o-chlorophenylurethane) plus 2,4-hexadiyn-1,6-diol bis(phenylurethane) |

Examples 37 to 42: Thermochromic Co-crystallized Acetylenic Compounds

The pairs of acetylenic compounds shown in the following table were mixed and dissolved in 100 ml of tetrahydrofuran. The solvent was evaporated out at about 60° C. under reduced pressure (about 10 mm) in a rotary evaporator within about 10 minutes. The residual solvent was removed under high vacuum at room temperature for 48 hrs. The co-crystallized acetylenic compounds were irradiated with $Co^{60}\gamma$-rays at room temperature in air for 50 Mrads. The copolymers were heated gradually on a Fisher-John's melting point apparatus. The temperature at which copolymers showed a color transition metallic (black) color to red color is shown in the table. The results indicate that in general the thermochromic transition temperature usually varies with the weight percent composition of the co-crystallized material. However, in some cases (Example 41) this variation is slight. The following designations are used for the acetylenic compounds:

1. DDDECMU—4,6-decadiyn-1,10-diol bis(ethoxycarbonylmethylurethane).
2. DDDBCMU—4,6-decadiyn-1,10-diol bis(n-butoxycarbonylmethylurethane).
3. 4DECMU—5,7-dodecadiyn-1,12-diol bis(ethoxycarbonylmethylurethane).
4. 4DBCMU—5,7-dodecadiyn-1,12-diol bis(n-butoxycarbonylmethylurethane).
5. DDDOTU—4,6-decadiyn-1,10-diol bis (o-tolylurethane).
6. DDDMTU—4,6-decadiyn-1,10-diol bis(m-tolylurethane).
7. DDDPTU—4,6-decadiyn-1,10-diol bis(p-tolylurethane).

TABLE VII

| Example No. | Composition | Weight of the Diacetylenes, G | | | | |
|---|---|---|---|---|---|---|
| 37 | DDDECMU | — | 0.2 | 0.5 | 0.8 | 1.0 |
|  | DDDBCMU | 1.0 | 0.8 | 0.5 | 0.2 | — |
|  | color transition temperature, °C. after 50 Mrads | 185 | 167 | 163 | — | 195 |
| 38 | DDDECMU | — | 0.2 | 0.5 | 0.8 | 1.0 |
|  | 4DECMU | 1.0 | 0.8 | 0.5 | 0.2 | — |
|  | color transition, temperature, °C., after 50 Mrads | 135 | 188 | 183 | 185 | 197 |
| 39 | DDDBCMU | — | 0.2 | 0.5 | 0.8 | 1.0 |
|  | 4DBCMU | 1.0 | 0.8 | 0.5 | 0.2 | — |
|  | color transition temperature, °C., after 50 Mrads | 112 | 174 | 168 | — | 185 |
| 40 | 4DECMU | — | 0.2 | 0.5 | 0.8 | 1.0 |
|  | 4DBCMU | 1.0 | 0.8 | 0.5 | 0.2 | — |
|  | color transition temperature, °C., after 50 Mrads | 105 | 110 | 115 | 120 | 135 |
| 41 | DDDOTU | 100 | 80 | 50 | 20 | 0 |
|  | DDDMTU | — | 20 | 50 | 80 | 100 |
|  | color transition, temperature, °C., after 50 Mrads | — | 195–205 | 195–205 | 205–210 | 195–197 |
| 42 | DDDMTU | 100 | 80 | 50 | 20 | — |
|  | DDDPTU | — | 20 | 50 | 80 | 100 |
|  | color transition, temperature, °C., after 50 Mrads | 195 | 250–255 | 265–270 | 280 | — |

Example 43: Molding of Copolymeric Acetylenic Compounds into Films

The following copolymeric pairs of acetylenic compounds listed in Table VIII were molded into thin films (about 5 mil thick) by the following procedure: two acetylenic compounds were dissolved in a solvent and the solvent was rapidly evaporated to yield a co-crystallized composition which was dried under reduced pressure; the resulting co-crystallized composition was irradiated with 50 Mrads of gamma radiation at room temperature to form a copolymeric composition and then treated with solvent to extract out unreacted monomer; the copolymeric compositon was then molded at a temperature above its melting point by compression molding at a pressure of about 15 tons to produce films. The films were pliable and reasonably strong and can be used in packaging and protective coating applications.

Films made from thermochromic copolymeric compositions can be used as temperature indicator devices. The acetylenic compounds were chosen such that the co-crystallized composition upon irradiation formed a copolymeric composition in which the decomposition temperature was at least about 20° C. above the melting point temperature. For example, the copolymer pair, DDDECMU/4DECMU in an 80/20 weight ratio of starting monomers, had a melting point of 185°–195° C., and a decomposition temperature of about 230°–260° C.; the copolymeric pair, DDDBCMU/4DBCMU in a 50/50 weight ratio of starting monomers, had a melting point of 170° to 175° C., and a decomposition temperature of about 222° to 240° C.

Direct Synthesis of Co-crystallizing Acetylenic Compounds

Example 44

In a three-necked flask fitted with a magnetic stirrer, an additional funnel and a thermometer, 11.0 g (0.1 mol) of 2,4-hexadiyn-1,6-diol and 300 ml of tetrahydrofuran were added. Also added was 1 g of di-t-butyl-tin-di-2-ethylhexanoate and 1 ml of triethylamine as catalysts. A solution of 4.95 g (0.025 mol) of p-bromophenyl isocyanate and 26.8 g (0.225 mol) of phenyl isocyanate in 100 ml of tetrahydrofuran was added dropwise from the addition funnel over a period of 1 hr. The reaction was allowed to proceed for 1 hr. Hexane was added to precipitate the mixture of the diacetylenes. The precipitate was filtered off quickly as it started turning pink and was redissolved in 100 ml of acetone. The mixture was stable in the solution.

This solution is referred to as HDDPBPUPU (10) in Example 47 below.

Example 45

In a three-necked flask fitted with a magnetic stirrer, an addition funnel and a thermometer 11.0 g (0.1 mol) of 2,4-hexadiyn-1,6-diol and 300 ml of tetrahydrofuran were added. Also added were 1 g of di-t-butyl-tin-di-2-ethylhexanoate and 1 ml of triethylamine as catalysts. A solution of 9.9 g (0.05 mol) of p-bromophenyl isocyanate and 23.8 g (0.2 mol) of phenyl isocyanate in 100 ml of tetrahydrofuran was added dropwise from the addition funnel over a period of 1 hr. The reaction was allowed to proceed for 1 hr. Hexane was added to precipitate the mixture of the diacetylenes. The precipitate was filtered off quickly and redissolved in 100 ml of acetone. The mixture of acetylenic compounds was stable in the solution. The solution is referred to as HDDPBPUPU (20) in Example 47.

Example 46

In a three-necked flask fitted with a magnetic stirrer, an addition funnel and a thermometer, 11.0 g (0.1 mol) of 2,4-hexadiyn-1,6-diol and 300 ml of tetrahydrofuran were added. Also added were 1 g of di-t-butyl-tin-di-2-ethylhexanoate and 1 g of triethylamine as catalysts. A solution of 14.85 g (0.075 mol) of p-bromophenyl isocyanate and 20.8 g (0.175 mol) of phenyl isocyanate in 100 ml of tetrahydrofuran was added dropwise from the addition funnel over a period of 1 hr. The reaction was allowed to proceed for 1 hr. Hexane was added to precipitate the mixture of the diacetylenes. The precipitate was filtered off and redissolved in 100 ml of acetone. The mixture of acetylenic compounds was stable in solution. This solution is referred to as HDDPBPUPU (30) in the following Example (Example 47).

Example 47

The solutions, HDDPBPUPU (10), (20) and (30) described in Examples 44, 45 and 46, respectively, were sprayed on Number 2 Whatman filter and solvent was evaporated. The following were the color developments, at room temperature, of the coated samples, for the indicated time.

| Time | Color of HDDPBPUPU | | |
|---|---|---|---|
| | (10) | (20) | (30) |
| 10 min | pink | slightly pink | almost white |
| 2 hrs | red (slightly violet) | pink | slightly pink |
| 24 hrs | violet | reddish pink | slightly pink |

TABLE VIII

| Copolymeric Pair | Original Concentration of Monomer % | Molding Temperature °C. | Color of the Film | Color of the Film After Transition | Color Transition Temperature Range °C. | |
|---|---|---|---|---|---|---|
| | | | | | During Heating | Reversible Transition During Cooling |
| 1. DDDECMU / 4DECMU | 80 / 20 | 200 | green gold | red | 150–160 | 145–140 |
| 2. DDDECMU / 4DECMU | 50 / 50 | 200 | black green gold | red | 150–155 | 145–140 |
| 3. DDDECMU / DDDBCMU | 50 / 50 | 170 | black green gold | red | 140–150 | 135–120 |
| 4. DDDECMU / DDDBCMU | 20 / 80 | 180 | black green gold | red | 160–168 | 140–135 |
| 5. DDDBCMU / 4DBCMU | 50 / 50 | 179 | green gold | red | 175–180 | 150–140 |
| 6. DDDBCMU / 4DBCMU | 20 / 80 | 180 | black green gold | red | 150–160 | 140–135 |
| 7. 4DECMU / 4DBCMU | 80 / 20 | 140 | red gold | orange | 80–95 | 70–50 |
| 8. 4DECMU / 4DBCMU | 50 / 50 | 120 | green gold (red) | orange | 80–95 | 70–50 |
| 9. 4DECMU / 4DBCMU | 20 / 80 | 120 | green gold (red) | orange | 80–95 | 70–50 |

Direct Synthesis of Co-crystallizing Acetylenic Compounds

Example 44

In a three-necked flask fitted with a magnetic stirrer, an additional funnel and a thermometer, 11.0 g (0.1 mol) of 2,4-hexadiyn-1,6-diol and 300 ml of tetrahydrofuran were added. Also added was 1 g of di-t-butyl-tin-di-2-ethylhexanoate and 1 ml of triethylamine as catalysts. A solution of 4.95 g (0.025 mol) of p-bromophenyl isocyanate and 26.8 g (0.225 mol) of phenyl isocyanate in 100 ml of tetrahydrofuran was added dropwise from the addition funnel over a period of 1 hr. The reaction was allowed to proceed for 1 hr. Hexane was added to precipitate the mixture of the diacetylenes. The precipitate was filtered off quickly as it started turning pink and was redissolved in 100 ml of acetone. The mixture was stable in the solution.

This solution is referred to as HDDPBPUPU (10) in Example 47 below.

Example 45

In a three-necked flask fitted with a magnetic stirrer, an addition funnel and a thermometer 11.0 g (0.1 mol) of 2,4-hexadiyn-1,6-diol and 300 ml of tetrahydrofuran were added. Also added were 1 g of di-t-butyl-tin-di-2-ethylhexanoate and 1 ml of triethylamine as catalysts. A solution of 9.9 g (0.05 mol) of p-bromophenyl isocyanate and 23.8 g (0.2 mol) of phenyl isocyanate in 100 ml of tetrahydrofuran was added dropwise from the addition funnel over a period of 1 hr. The reaction was allowed to proceed for 1 hr. Hexane was added to precipitate the mixture of the diacetylenes. The precipitate was filtered off quickly and redissolved in 100 ml of acetone. The mixture of acetylenic compounds was stable in the solution. The solution is referred to as HDDPBPUPU (20) in Example 47.

Example 46

In a three-necked flask fitted with a magnetic stirrer, an addition funnel and a thermometer, 11.0 g (0.1 mol) of 2,4hexadiyn-1,6-diol and 300 ml of tetrahydrofuran were added. Also added were 1 g of di-t-butyl-tin-di-2-ethylhexanoate and 1 g of triethylamine as catalysts. A solution of 14.85 g (0.075 mol) of p-bromophenyl isocyanate and 20.8 g (0.175 mol) of phenyl isocyanate in 100 ml of tetrahydrofuran was added dropwise from the addition funnel over a period of 1 hr. The reaction was allowed to proceed for 1 hr. Hexane was added to precipitate the mixture of the diacetylenes. The precipitate was filtered off and redissolved in 100 ml of acetone. The mixture of acetylenic compounds was stable in solution. This solution is referred to as HDDPBPUPU (30) in the following Example (Example 47).

Example 47

The solutions, HDDPBPUPU (10), (20) and (30) described in Examples 44, 45 and 46, respectively, were sprayed on Number 2 Whatman filter and solvent was evaporated. The following were the color developments, at room temperature, of the coated samples, for the indicated time.

| Time | Color of HDDPBPUPU | | |
|---|---|---|---|
| | (10) | (20) | (30) |
| 10 min | pink | slightly pink | almost white |
| 2 hrs | red (slightly violet) | pink | slightly pink |
| 24 hrs | violet | reddish pink | slightly pink |

I claim:

1. A process for producing a co-crystallized composition of at least two different acetylenic compounds, each containing at least one —C≡C—C≡C— group and substituents selected from the group consisting of sulfonate, urethane and alcohol radicals, at least one of said compounds being capable of undergoing a contrasting color change upon exposure to ultraviolet radiation, gamma radiation, or electron beam, or to thermal annealing; which composition exhibits a substantially different thermogram than the sum of the thermograms of the individual components as obtained by differential scanning calorimetry; said process consisting essentially of forming a solution of said different acetylenic compounds and recovering said co-crystallized composition from the solution by rapidly and substantially decreasing the solubility of said composition in the solution to thereby obtain co-crystallization before crystallization of the acetylenic compounds separately, by using a means of the groups consisting of (a) fast removal of solvent and (b) rapid mixing of the solution with about 1 to 10 parts, per part of solvent, of a liquid which is miscible with the solvent but is a non-solvent for the co-crystallized composition.

2. Process of claim 1 wherein said removal of solvent is accomplished by rapid spray drying while depositing said composition upon a substrate.

3. Process of claim 1 wherein the solubility of said composition in the solution is decreased by rapidly adding the solution with stirring to said non-solvent liquid, said stirring being adequate to insure complete conversion of the acetylenic compounds to a co-crystallized composition.

* * * * *